(12) United States Patent
Sirch et al.

(10) Patent No.: US 7,307,194 B2
(45) Date of Patent: Dec. 11, 2007

(54) METHOD FOR PRODUCING 1, 6 HEXANE DIOL

(75) Inventors: Tilman Sirch, Schifferstadt (DE); Gerd-Dieter Tebben, Goettingen (DE); Ludwig E. Heck, Edingen-Neckarhausen (DE); Armin Diefenbacher, Germersheim (DE); Alfred Krause, Speyer (DE); Franz Borgel, Dirmstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/580,685

(22) PCT Filed: Oct. 27, 2005

(86) PCT No.: PCT/EP2005/011489

§ 371 (c)(1),
(2), (4) Date: May 26, 2006

(87) PCT Pub. No.: WO2006/048170

PCT Pub. Date: May 11, 2006

(65) Prior Publication Data

US 2007/0112225 A1    May 17, 2007

(30) Foreign Application Priority Data

Nov. 5, 2004  (DE) .................. 10 2004 054 047

(51) Int. Cl.
  *C07C 31/20*  (2006.01)
(52) U.S. Cl. .............. 568/853; 568/852; 568/854; 568/864
(58) Field of Classification Search ............ 568/853, 568/854, 852, 864
  See application file for complete search history.

(56) References Cited

FOREIGN PATENT DOCUMENTS

| | | |
|---|---|---|
| EP | 0 552 463 | 7/1993 |
| WO | 97/31882 | 9/1997 |
| WO | 97/31883 | 9/1997 |

OTHER PUBLICATIONS

"Ullmann's Encyclopedia of Industrial Chemistry", Fifth, Completely Revised Edition, vol. A8, p. 49 1987.
Weyl, Houben, "Methoden Der Organischen Chemie", Band IV1c, pp. 45-67, 1980.
Weyl, Houben, "Methoden Der Organischen Chemie", Band IV1c, pp. 16-26, 1980.

*Primary Examiner*—Elvis O. Price
(74) *Attorney, Agent, or Firm*—Oblon, Spivak, McClelland, Maier & Neustadt, P.C.

(57) ABSTRACT

The present invention provides a process for preparing 1,6-hexanediol from a carboxylic acid mixture which comprises adipic acid, 6-hydroxycaproic acid and small amounts of 1,4-cyclohexanediols and is obtained as a by-product in the oxidation of cyclohexane to cyclohexanone/cyclohexanol with oxygen or oxygen-containing gases and by water extraction of the reaction mixture, by esterification of the acids and hydrogenation, in which a) the mono- and dicarboxylic acids present in the aqueous dicarboxylic acid mixture are reacted with a low molecular weight alcohol to give the corresponding carboxylic esters,
  b) the resulting esterification mixture is freed of excess alcohol and low boilers in a first distillation stage,
  c) a separation of the bottom product is carried out in a second distillation stage into an ester fraction substantially free of 1,4-cyclohexanediols and a fraction comprising at least the majority of the 1,4-cyclohexanediols,
  d) the ester fraction substantially free of 1,4-cyclohexanediols is catalytically hydrogenated and
  e) 1,6-hexanediol is obtained in a purifying distillation stage from the hydrogenation effluent while removing an alcohol-low boiler mixture in a manner known per se, wherein alcohol is removed by a membrane system from the mixtures, obtained after the esterification in stage b) and/or after the hydrogenation in stage e), of alcohols and low boilers and recycled into the esterification.

6 Claims, 2 Drawing Sheets

METHOD FOR PRODUCING 1, 6 HEXANE DIOL

Figure 1:
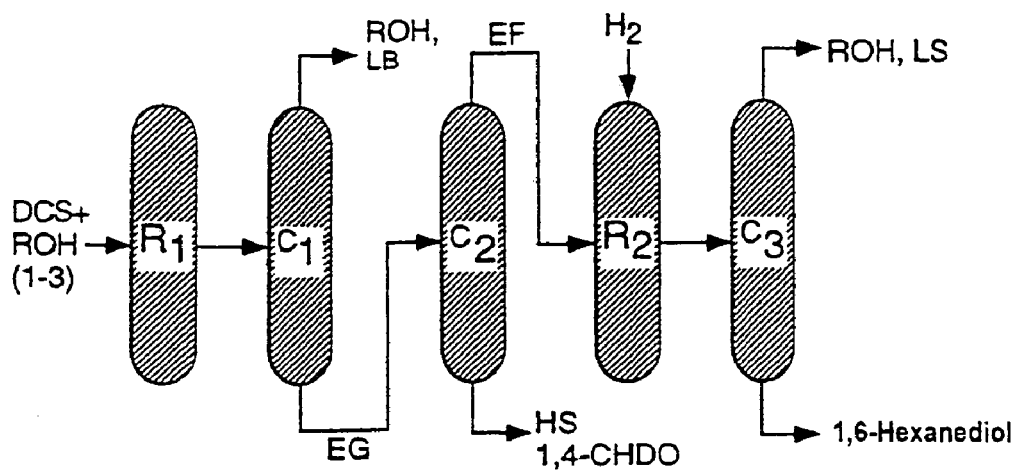

The invention relates to a process for preparing 1,6-hexanediol from a carboxylic acid mixture which comprises adipic acid and 6-hydroxycaproic acid and is obtained in the oxidation of cyclohexane to cyclohexanone/cyclohexanol with oxygen and by water extraction of the reaction mixture, by esterification of the acids with $C_1$- to $C_{10}$-alcohols and hydrogenation, wherein alcohol is removed by a membrane system from the mixture, obtained after the esterification and/or after the hydrogenation, of esterification alcohol and low boilers and recycled into the esterification.

WO 97/31883 discloses a process for preparing 1,6-hexanediol from aqueous solutions of carboxylic acids which are obtained in the oxidation of cyclohexane to cyclohexanone/cyclohexanol with oxygen and water extraction, in which a) the mono- and dicarboxylic acids present in the aqueous dicarboxylic acid mixture are reacted with a low molecular weight alcohol to give the corresponding carboxylic esters,
b) the resulting esterification mixture is freed of excess alcohol and low boilers in a first distillation stage,
c) a separation of the bottom product is carried out in a second distillation stage into an ester fraction substantially free of 1,4-cyclohexanediols and a fraction comprising at least the majority of the 1,4-cyclohexanediols,
d) the ester fraction substantially free of 1,4-cyclohexanediols is catalytically hydrogenated and
e) 1,6-hexanediol is obtained in a purifying distillation stage from the hydrogenation effluent while removing an alcohol-low boiler mixture in a manner known per se.

The aqueous solutions of carboxylic acids which are formed as by-products in the oxidation of cyclohexane to cyclohexanol and cyclohexanone (cf. Ullmann's Encyclopedia of Industrial Chemistry, 5th ed., 1987, Vol. A8, p. 49), referred to hereinbelow as dicarboxylic acid solution (DCS), comprise (calculated anhydrously in % by weight) generally between 10 and 40% adipic acid, between 10 and 40% 6-hydroxycaproic acid, between 1 and 10% glutaric acid, between 1 and 10% 5-hydroxyvaleric acid, between 1 and 5% 1,2-cylcohexanediols, between 1 and 5% 1,4-cyclohexanediols, between 2 and 10% formic acid, and a multitude of further mono- and dicarboxylic acids, esters, oxo and oxa compounds, whose individual contents generally do not exceed 5%. Examples include acetic acid, propionic acid, butyric acid, valeric acid, caproic acid, oxalic acid, malonic acid, succinic acid, 4-hydroxybutyric acid and γ-butyrolactone.

In order to operate the process according to WO 97/31883 with maximum economic viability, it is sensible to recover the esterification alcohol ROH and to always reuse it in the esterification, i.e. to bring about a low alcohol input number.

The esterification alcohol is recovered in two stages of the process and is in each case obtained in a mixture with low boilers. In stage b) of the process, after the esterification, an alcohol-low boiler mixture is recovered and generally consists of about 80% by weight of esterification alcohol, 10% by weight of water and a residue consisting of low-boiling esters and ethers. After the hydrogenation in stage e), an alcohol-low boiler mixture is obtained and consists to an extent of about 80% by weight of the esterification alcohol and 5% by weight of low-boiling ethers, and a residue of further alcohols.

The low-boiling ether fraction is composed substantially of 2-methyltetrahydropyran (mTHP), tetrahydropyran (THP), 2-methyltetrahydrofuran (mTHF), 2-ethyltetrahydrofuran (ETHF), tetrahydrofuran (THF) and hexamethylene oxide. The recycling of these components into the esterification would lead to an accumulation of the ether components in the esterification alcohol, which leads to increased energy demands in the downstream column and too low an alcohol excess, and thus to a poorer conversion in the esterification.

To prevent this accumulation of ether components, according to WO 97/31883, the alcohol-low boiler mixtures from stages b) and/or e) are subjected to a distillation in a column. A disadvantage of this process is that the removal of the ethers is found to be incomplete. It therefore becomes necessary, especially in continuous operation of the hexanediol preparation process, in spite of the distillation, to discharge a portion of the recovered alcohol (return alcohol) and replace it with fresh esterification alcohol. In continuous mode, the discharged portion of the return alcohol is about 2.2% by weight of the return alcohol fed to the esterification. The discharged portion of the return alcohol is generally incinerated in an expensive manner.

It is therefore an object of the present invention to propose a process which avoids the disadvantages mentioned.

According to the invention, this object is achieved by a process for preparing 1,6-hexanediol from a carboxylic acid mixture which comprises adipic acid, 6-hydroxycaproic acid and small amounts of 1,4-cyclohexanediols and is obtained as a by-product in the oxidation of cyclohexane to cyclohexanone/cyclohexanol with oxygen or oxygen-containing gases and by water extraction of the reaction mixture, by esterification of the acids and hydrogenation, in which a) the mono- and dicarboxylic acids present in the aqueous dicarboxylic acid mixture are reacted with a low molecular weight alcohol to give the corresponding carboxylic esters,
b) the resulting esterification mixture is freed of excess alcohol and low boilers in a first distillation stage,
c) a separation of the bottom product is carried out in a second distillation stage into an ester fraction substantially free of 1,4-cyclohexanediols and a fraction comprising at least the majority of the 1,4-cyclohexanediols;
d) the ester fraction substantially free of 1,4-cyclohexanediols is catalytically hydrogenated and
e) 1,6-hexanediol is obtained in a purifying distillation stage from the hydrogenation effluent while removing an alcohol-low boiler mixture in a manner known per se, wherein alcohol is removed by a membrane system from the mixtures, obtained after the esterification in stage a) and/or after the hydrogenation in stage e), of alcohols and low boilers, and recycled fully or partly, but preferably fully, into the esterification.

The inventive removal of the alcohol-low boiler mixture with the membrane system enables the prevention of the accumulation of the ether fraction when the esterification alcohol is recycled by a more effective removal of the ether. The return alcohol discharge for the incineration of the alcohol can generally be lowered from about 2.2% by weight in the distillation process known in WO 97/31883 to 0.6% by weight. The process according to the invention is distinctly more economically viable as a result of the saving of esterification alcohol and incineration costs, which is a considerable advantage especially for industrial scale plants.

Apart from the inventive separation of the alcohol-low boiler mixture with the aid of a membrane system, the process according to the invention is described in all details in WO 97/31883, so that reference is made explicitly to this document. All statements made there shall also apply here without any restrictions.

The process described there with its variants A (FIG. 1) and variant B (FIG. 2) is illustrated once again here (the terms overhead and as bottoms each referring to withdrawal above and below the feed respectively):

Variant A

As shown in FIG. 1, the dicarboxylic acid solution (DCS), if appropriate after dewatering, is fed together with a $C_1$- to $C_3$-alcohol, preferably methanol, into the esterification reactor $R_1$ where the carboxylic acids are esterified. The resulting esterification mixture then passes into column $C_1$ in which the excess alcohol (ROH), water and low boilers (LB) are distilled off overhead and the ester mixture (EM) is drawn off as bottoms and fed into the fractionating column $C_2$. In this column, the mixture is fractionated into an ester fraction (EF) substantially free of 1,4-cyclohexanediols and bottom fraction consisting of high boilers (HB) and 1,4-cyclohexanediols (1,4-CHDO). The ester fraction (EF) is then catalytically hydrogenated in the hydrogenation reactor $R_2$ and the hydrogenation mixture is separated in the distillation column $C_3$ into alcohol (ROH), low boilers (LB) and pure 1,6-hexanediol.

Variant B

Figure 2:
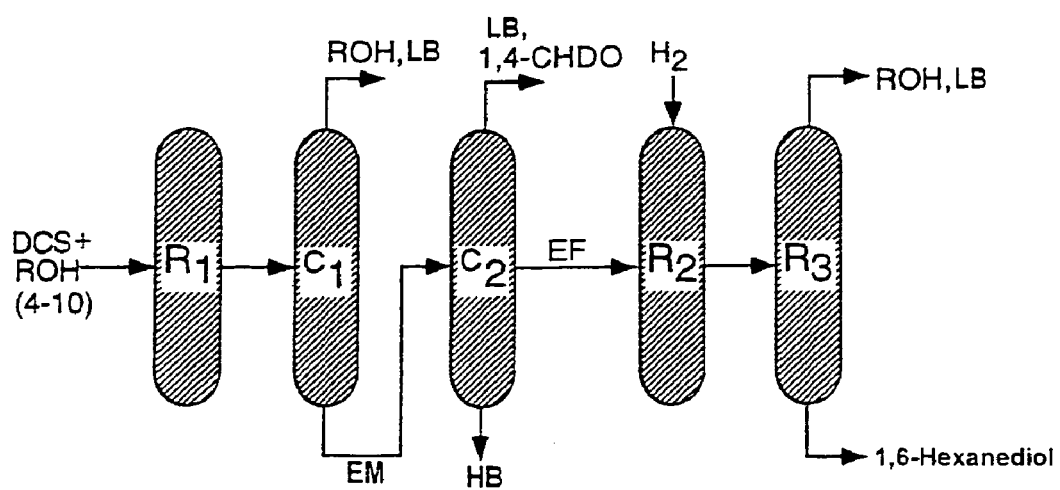

When alcohols having 4 and more carbon atoms are used for the esterification, especially n- or i-butanol, the process according to FIG. 2 differs only in that the ester mixture (EM) is separated in the fractionating column $C_2$ into a top product of low boilers (LB) which comprise the 1,4-cyclohexanediols (1,4-CHDO) and an ester fraction (EF) which is substantially free of 1,4-cyclohexanediol and is obtained as a side fraction or as bottoms comprising the ester fraction and fed into the hydrogenation stage ($R_2$).

Figure 3:
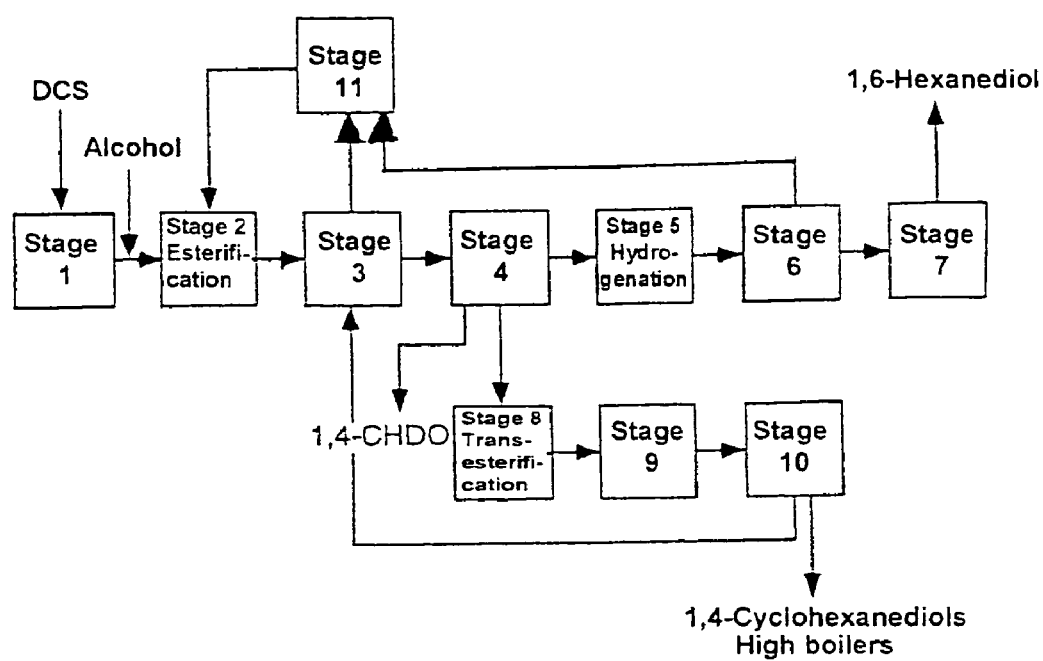

The process is illustrated in further detail hereinbelow. In FIG. 3, the individual process steps are broken down into further stages, stages 2, 2a, 3, 4, 5, 6, 7 being essential for the process, and stages 3 and 4, and 6 and 7, also being combinable. Stages 8, 9, 10 and 11 are optional, but in some cases sensible to increase the economic viability of the process.

The dicarboxylic acid solution (DCS) is generally an aqueous solution having a water content of from 20 to 80%. Since an esterification reaction constitutes an equilibrium reaction, it is usually sensible, especially in the case of esterification with, for example, methanol, to remove water present before the reaction, in particular when water is not to be removed, for example not to be removed azeotropically, during the esterification reaction. The dewatering in stage 1 may be effected, for example, with a membrane system, or preferably by a distillation apparatus in which water is removed overhead and higher monocarboxylic acids, dicarboxylic acids and 1,4-cyclohexanediols are removed via the bottom at from 10 to 250° C., preferably from 20 to 200° C., more preferably from 30 to 200° C., and a pressure of from 1 to 1500 mbar, preferably from 5 to 1100 mbar, more preferably from 20 to 1000 mbar. The bottom temperature is preferably selected such that the bottom product can be drawn off in liquid form. The water content in the bottom of the column may be from 0.01 to 10% by weight, preferably from 0.01 to 5% by weight, more preferably from 0.01 to 1% by weight.

The water may be removed in such a way that the water is obtained predominantly acid-free, or the lower monocarboxylic acids present in the DCS, substantially formic acid, can for, most part be distilled off with the water, so that they cannot bind any esterification alcohol in the esterification.

An alcohol having from 1 to 10 carbon atoms is added to the carboxylic acid stream from stage 1, in variant A alcohols having from 1 to 3 carbon atoms, i.e. methanol, ethanol, propanol or isopropanol, preferably methanol, in variant B alcohols having from 4 to 10, in particular from 4 to 8; carbon atoms, and more preferably n-butanol, isobutanol, n-pentanol and i-pentanol.

The mixing ratio of alcohol to carboxylic acid stream (mass ratio) may be from 0.1 to 30, preferably from 0.2 to 20, more preferably from 0.5 to 10.

This mixture passes as a melt or solution into the reactor of stage 2, in which the carboxylic acids are esterified with the alcohol. The esterification reaction may be carried out at from 50 to 400° C., preferably at from 70 to 300° C., more preferably at from 90 to 200° C. It is possible to apply an external pressure, but preference is given to carrying out the esterification under the autogenous pressure of the reaction system. The esterification apparatus used may be a stirred tank or flow tube, or a plurality of each may be used. The residence time needed for the esterification is between 0.3 and 10 hours, preferably from 0.5 to 5 hours. The esterification reaction may proceed without addition of a catalyst; however, preference is given to adding a catalyst to increase the reaction rate. The catalyst may be a homogeneously dissolved or a solid catalyst. Examples of homogeneous catalysts include sulfuric acid, phosphoric acid, hydrochloric acid, sulfonic acids such as p-toluenesulfonic acid, heteropolyacids such as tungstophosphoric acid, or Lewis acids such as aluminum, vanadium, titanium, boron compounds. Preference is given to mineral acids, especially sulfuric acid. The weight ratio of homogeneous catalysts to carboxylic acid melt is generally from 0.0001 to 0.5, preferably from 0.001 to 0.3.

Suitable solid catalysts are acidic or superacidic materials, for example acidic and superacidic metal oxides such as $SiO_2$, $Al_2O_3$, $SnO_2$, $ZrO_2$ or sheet silicates or zeolites, all of which may be doped with mineral acid residues such as sulfate or phosphate to increase the acid strength, or organic ion exchangers having sulfonic acid or carboxylic acid groups. The solid catalysts may be arranged as a fixed bed or used as a suspension.

The water formed in the reaction is appropriately removed continuously, for example through a membrane or distillatively.

The completeness of the conversion of the free carboxyl groups present in the carboxylic acid melt is determined with the acid number (mg KOH/g) measured after the reaction. Subtracting any acid added as a catalyst, it is from 0.01 to 50, preferably from 0.1 to 10. Not all carboxyl groups present in the system are present as esters of the alcohol used, but rather a portion may be present in the form of dimeric or oligomeric esters, for example with the OH end of the hydroxycaproic acid.

The esterification mixture is fed into stage 3, a membrane system or preferably a distillation column. When a dissolved acid has been used as a catalyst for the esterification reaction, the esterification mixture is appropriately neutralized with a base, in which case from 1 to 1.5 base equivalents are added per acid equivalent of the catalyst. The bases used are generally alkali metal or alkaline earth metal oxides, carbonates, hydroxides or alkoxides, or amines in substance or dissolved in the esterification alcohol.

When a column is used in stage 3, the feed to the column is preferably between the top and the bottom stream. The excess esterification alcohol ROH, water and, for example, corresponding esters of formic acid, acetic acid and propionic acid are drawn off overhead at pressures of from 1 to 1500 mbar, preferably from 20 to 1000 mbar, more preferably from 40 to 800 mbar, and temperatures between 0 and 150° C., preferably 15 and 90° C., and in particular 25 and 75° C. This stream may either be incinerated or preferably worked up further in stage 11.

The bottoms obtained are an ester mixture which consists predominantly of the esters of the alcohol ROH used with dicarboxylic acids such as adipic acid and glutaric acid, hydroxycarboxylic acids such as 6-hydroxycaproic acid and 5-hydroxyvaleric acid, and of oligomers and free or esterified 1,4-cyclohexanediols. It may be sensible to permit a residual content of water and/or alcohol ROH up to in each case 10% by weight in the ester mixture. The bottom temperatures are from 70 to 250° C., preferably from 80 to 220° C., more preferably from 100 to 190° C.

The stream from stage 3, which has been freed predominantly of water and esterification alcohol ROH, is fed into stage 4. This is a distillation column in which the feed is generally effected between the low-boiling components and the high-boiling components. The column is operated at temperatures of from 10 to 300° C., preferably from 20 to 270° C., more preferably from 30 to 250° C., and pressures of from 1 to 1000 mbar, preferably from 5 to 500 mbar, more preferably from 10 to 200 mbar.

In variant A, i.e. the esterification with $C_1$- to $C_3$-alcohols, especially methanol, the stream from stage 3 is then separated into a top fraction to be hydrogenated and a bottom fraction comprising the 1,4-cyclohexanediols.

The top fraction consists predominantly of residual water and residual alcohol ROH, esters of the alcohol ROH with monocarboxylic acids, predominantly $C_3$- to $C_6$-monocarboxylic acids, esters with hydroxycarboxylic acids such as 6-hydroxycaproic acid, 5-hydroxyvaleric acid, and in particular the diesters with dicarboxylic acids such as adipic acid, glutaric acid and succinic acid, and also 1,2-cyclohexanediols, caprolactone and valerolactone.

The components mentioned may be removed together overhead and fed into the hydrogenation (stage 5) or, in a further preferred embodiment, separated in the column into a-top stream which comprises predominantly residual water and residual alcohol and the abovementioned esters of the $C_3$- to $C_5$-carboxylic acids, and a sidestream which comprises predominantly the abovementioned esters of the $C_6$-carboxylic acids and dicarboxylic acids which then pass into the hydrogenation.

The high-boiling components of the stream from stage 4, consisting predominantly of 1,4-cyclohexanediols or esters thereof, dimeric or oligomeric esters and constituents of the DCS, some of them polymeric, which are not defined in more detail, are removed via the stripping section of the column. These may be obtained together or in such a way that predominantly the 1,4-cyclohexanediols are removed in the stripping section via a sidestream of the column and the remainder is removed via the bottom. The thus obtained 1,4-cyclohexanediols may find use, for example, as a starting material for active ingredients. The high-boiling components, with or without the content of 1,4-cyclodiols, may either be incinerated or, in a preferred embodiment, pass into stage 8 for the transesterification.

In variant B, i.e. the esterification with $C_4$- to $C_{10}$-alcohols, in particular n- or i-butanol, the stream from stage 3 may be separated in stage 4 into a top fraction comprising the 1,4-cyclohexanediols, a sidestream comprising predominantly the $C_6$ esters, which passes into the hydrogenation, and a bottom stream comprising high boilers, which can if appropriate pass into stage 8.

The top fraction consists predominantly of residual alcohol ROH, $C_1$- to $C_3$-monoesters of the alcohol ROH, valerolactone and 1,2- and 1,4-cyclohexanediols.

The sidestream comprises predominantly diesters of succinic acid, glutaric acid and adipic acid, and monoesters of 5-hydroxyvaleric acid and 6-hydroxycaproic acid. This sidestream may be withdrawn either above or else below the feed point of the column and fed into the hydrogenation (stage 5).

Analogously to variant A, the bottom stream comprising oligomeric esters and other high boilers may either be incinerated or advantageously pass into stage 8.

In a further embodiment, the $C_6$ esters in stage 4 are removed together with either the bottom stream and then, in a further column, either removed as the bottom product from the top fraction already described, which consists predominantly of residual alcohol ROH, $C_1$- to $C_3$-monoesters of the alcohol ROH, valerolactone and 1,2- and 1,4-cyclohexanediols, or as the top stream from the high boilers.

The fraction of stage 4, which is free or virtually free of 1,4-cyclohexanediols, either the entire stream or the sidestream comprising mainly esters of $C_6$ acids, is passed into the hydrogenation stage 5.

Stages 3 and 4, especially when only relatively small amounts are processed, may be combined. To this end, for example, the $C_6$ ester stream may be obtained in a batchwise fractional distillation, again without 1,4-cyclohexanediols passing into the stream conducted to the hydrogenation.

The hydrogenation is effected catalytically either in the gas or liquid phase. Useful catalysts are in principle all homogeneous and heterogeneous catalysts suitable for the hydrogenation of carbonyl groups, such as metals, metal oxides, metal compounds or mixtures thereof. Examples of homogeneous catalysts are described, for example, in Houben-Weyl, Methoden der Organischen Chemie [Methods of Organic Chemistry], volume IV/1c, Georg Thieme Verlag Stuttgart, 1980, p. 45-67) and examples of heterogeneous catalysts are described, for example, in Houben-Weyl, Methoden der Organischen Chemie, volume IV/1c, p. 16 to 26.

Preference is given to using catalysts which comprise one or more elements from transition groups I and VI to VIII of the Periodic Table of the Elements, preferably copper, chromium, molybdenum, manganese, rhenium, ruthenium, cobalt, nickel and palladium, more preferably copper, cobalt or rhenium.

The catalysts may consist of the active components alone or the active components may be applied to supports. Suitable support materials are, for example, $Cr_2O_3$, $Al_2O_3$, $SiO_2$, $ZrO_2$, $ZnO_2$, BaO and MgO or mixtures thereof.

Particular preference is given to catalysts as described in EP 0 552 463. These are catalysts which, in the oxidic form, have the composition $$Cu_aAl_bZr_cMn_dO_x$$

where a>0, b>0, c=0, d>0, a>b/2, b>a/4, a>c and a>d, and x is the number of oxygen ions required per formula unit to preserve electronic neutrality. These catalysts can be prepared, for example, according to the details of EP 552 463, by precipitation of sparingly soluble compounds from solutions which comprise the appropriate metal ions in the form of their salts. Suitable salts are, for example, halides, sulfates and nitrates. Suitable precipitants are all agents which lead to the formation of those insoluble intermediates which can be converted to the oxides by thermal treatment. Particularly suitable intermediates are the hydroxides and carbonates or hydrogencarbonates, so that precipitants used with particular preference are alkali metal carbonates or ammonium carbonate. It is important for the preparation of the catalysts that the intermediates are thermally treated at temperatures between 500° C. and 1000° C. The BET surface area of the catalysts is between 10 and 150 m$^2$/g.

Preference is given to using heterogeneous catalysts which are used either in fixed bed form or as a suspension. When the hydrogenation is carried out in the gas phase and over fixed bed catalyst, temperatures of from 150 to 300° C. at pressures of from 1 to 100 bar, preferably from 15 to 70 bar, are generally employed. It is appropriate that the amount of hydrogen used as a hydrogenating agent and carrier gas is at least enough to render reactants, intermediates and products liquid during the reaction. The excess hydrogen is preferably circulated, and a small portion may be discharged as offgas to remove inerts, for example methane. It is possible for one reactor or a plurality of reactors connected in series to be used.

When the hydrogenation is effected in the liquid phase with fixed bed or suspended catalyst, it is generally carried out at temperatures between 100 and 350° C., preferably 120 and 300° C. and pressures of from 30 to 350 bar, preferably from 40 to 300 bar.

The hydrogenation may be carried out in one reactor or a plurality of reactors connected in series. The hydrogenation in the liquid phase over a fixed bed can be carried out both in trickle and liquid phase mode. In a preferred embodiment, a plurality of reactors is used, in which case the predominant portion of the ester is hydrogenated in the first reactor and the first reactor is preferably operated with liquid circulation for heat removal and the downstream reactor or reactors are preferably operated without circulation for completion of the conversion.

The hydrogenation may be effected batchwise, preferably continuously.

The hydrogenation effluent consists substantially of 1,6-hexanediol and the alcohol ROH. Further constituents are, in particular if the entire low-boiling stream of stage 4 has been used as per variant A, 1,5-pentanediol, 1,4-butanediol, 1,2-cyclohexanediols and small amounts of monoalcohols having from 1 to 6 carbon atoms and water.

This hydrogenation effluent is separated in stage 6, which is, for example, a membrane system or preferably a distillation column, into the alcohol ROH which additionally comprises the majority of the further low-boiling components and a stream which comprises predominantly 1,6-hexanediol in addition to 1,5-pentanediol and the 1,2-cyclohexanediols. In this separation, top temperatures of from 0 to 120° C., preferably from 20 to 100° C., more preferably from 30 to 90° C., and bottom temperatures of from 100 to 270° C., preferably from 140 to 260° C., more preferably from 160 to 250° C., are established at a pressure of from 10 to 1500 mbar, preferably from 30 to 1200 mbar, more preferably from 50 to 1000 mbar. The low-boiling stream may be recycled either directly into the esterification of stage 2, or pass into stage 8 or into stage 11.

The 1,6-hexanediol-containing stream is purified in a column in stage 7. In this purification, 1,5-pentanediol, if appropriate the 1,2-cyclohexanediols, and any further low boilers present are removed overhead. When the 1,2-cyclohexanediols and/or 1,5-pentanediol are to be obtained as additional products of value, they may be separated in a further column. Any high boilers present are discharged via the bottom. 1,6-Hexanediol is withdrawn from a sidestream of the column with a purity of at least 99%. Top temperatures of from 50 to 200° C., preferably from 60 to 150° C., and bottom temperatures of from 130 to 270° C., preferably from 150 to 250° C., are established at pressures of from 1 to 1000 mbar, preferably from 5 to 800 mbar, more preferably from 20 to 500 mbar.

When only relatively small amounts of 1,6-hexanediol are to be prepared, stages 6 and 7 may also be combined in a batchwise fractional distillation.

In order to operate the hexanediol preparation in a very economical manner, it is sensible to recover the esterification alcohol ROH and always reuse it for the esterification. To this end, the stream, comprising predominantly the alcohol ROH, for example methanol, from stage 3 and/or 6 may be worked up in stage 11. For this purpose, a membrane system is used in accordance with the invention. Membrane separation may be performed in a manner known per se as reverse osmosis, pervaporation or vapor permeation, of which preference is given to reverse osmosis. The basic principles and the typical use conditions of these membrane separation operations are described, for example, in T. Melin, R. Rautenbach, Membranverfahren—Grundlagen der Modul- und Anlagenauslegung [Membrane Processes—Basics of Module and System Design], Springer-Verlag Berlin Heidelberg, 2nd edition, 2004, or in R. Baker, Membrane Technology and Applications, John Wiley & Sons, 2nd Edition, 2004.

In the reverse osmosis preferred in accordance with the invention, the mixture to be separated flows along the membrane under a pressure of from 40 to 300 bar. The permeate passes through the membrane. The maximum achievable concentration in the retentate is determined by the osmotic pressure of the retained species. The membranes used are membranes having pore-free polymeric separation layers. Useful membrane polymers are any which are stable in the process medium under the specified separation conditions. The membranes may be designed in flat, pillow, tubular, multichannel element, capillary or wound geometry, for which the corresponding pressure casings which allow separation between retentate and the permeate are available. In addition, a plurality of these elements may be combined in one casing to give a module. The flow-through rate in the module is between 0.05 and 8 m/s, more preferably between 0.1 and 4 m/s. The transmembrane pressure differential between permeate and retentate space is from 20 to 200 bar, preferably between 40 and 100 bar in the claimed process. The temperature of the feed stream, i.e. the stream, comprising predominantly the alcohol ROH, for example methanol, from stage 3 and/or stage 6 to the membrane separation unit is between 20 and 90° C.

In a further preferred embodiment of the process, the high-boiling stream from stage 4 (as per variant A) is used to increase the total yield of 1,6-hexanediol based on adipic acid and 6-hydroxycaproic acid used in the DCS used. To this end, the proportion of dimeric and oligomeric esters of adipic acid or hydroxycaproic acid is reacted in stage 8 with further amounts of the alcohol ROH in the presence of a catalyst. The weight ratio of alcohol ROH and the bottom stream from stage 4 is between 0.1 to 20, preferably from 0.5 to 10, more preferably from 1 to 5. Suitable catalysts are in principle those already described for the esterification in stage 2. However, preference is given to using Lewis acids. Examples thereof are compounds or complexes of aluminum, tin, antimony, zirconium or titanium, such as zirconium acetylacetonate or tetraalkyl titanates, e.g. tetraisopropyl titanate, which are employed in concentrations of from 1 to 10 000 ppm, preferably from 50 to 6000 ppm, more preferably from 100 to 4000 ppm, based on the transesterification mixture. Particular preference is given in this context to titanium compounds.

The transesterification may be carried out batchwise or continuously, in one reactor or a plurality of reactors, stirred tanks or tubular reactors connected in series, at temperatures between 100 and 300° C., preferably from 120 to 270° C., more preferably from 140 to 240° C., and the autogenous pressures which are established. The required residence times are from 0.5 to 10 hours, preferably from 1 to 4 hours.

In the case of esterification with methanol, this stream from stage 8 can, for example, be fed back into stage 3. To prevent accumulations, in particular of 1,4-cyclohexanediols, a substream of the high boilers from stage 4 then has to be discharged batchwise or continuously. Another possibility is to recycle the stream from stage 8 not into stage 3, but rather, to separate it, analogously to stage 3, in a stage 9 into predominantly alcohol ROH which may then passes back into stage 2, 8 or 11, and a stream which comprises the esters.

This ester stream may in principle (with the proviso of the prevention of accumulations of the 1,4-cyclohexanediols) be recycled into stage 4, or is preferably separated in a further stage 10 into the esters of the $C_6$ acids and, in rather insignificant amounts, into the esters of the $C_5$ acids on the one hand, which may either be fed into stage 4 or directly into stage 5, and high boilers on the other hand, which comprise the 1,4-cyclohexanediols, whereupon the high boilers are discharged.

In this way, yields of 1,6-hexanediol of over 95% are achieved at purities of over 99%.

The inventive separation of the alcohol-low boiler mixtures allows the process according to WO 97/31883 to be carried out in a more economical manner, since a distinctly higher proportion of the esterification alcohol can be recycled into the esterification.

The process is illustrated in detail but in no way restricted with reference to the example which follows.

EXAMPLE VARIANT A

Stage 1 (Dewatering):

0.1 kg of dicarboxylic acid solution (consisting substantially of adipic acid, 6-hydroxycaproic acid, 1,4-cyclohexanediols, glutaric acid, 5-hydroxyvaleric acid, formic acid, water and with a residual cobalt content of <1 ppm) was distilled continuously in a distillation apparatus (three-tray bubble-cap tray column with external oil heating circuit, oil temperature 150° C., tray volume in each case approx. 25 ml, feed via the bubble-cap trays), with attached column having random packing (approx. 4 theoretical plates, no reflux at the top). The top product obtained was 0.045 kg/h with a formic acid content in the water of approx. 3%. In the bottom stream (5.5 kg), the water content was approx. 0.4%.

Stage 2 (Esterification):

5.5 kg of the bottom stream from stage 1 were reacted with 8.3 kg/h of methanol and 14 g/h of sulfuric acid continuously in a tubular reactor (I 0.7 m, O 1.8 cm, residence time 2.7 h). The acid number of the effluent minus sulfuric acid was approx. 10 mg KOH/g.

Stage 3 (Removal of Excess Alcohol and of Water):

In a 20 cm column having random packing, the esterification stream from stage 2 was distilled (1015 mbar, top temperature 65° C., bottom temperature up to 125° C.). 7.0 kg were drawn off overhead. As the bottom product, 6.8 kg were obtained.

Stage 4 (Fractionation; 1,4-Cyclohexanediol Removal):

In a 50 cm column having random packing, the bottom stream from stage 3 was fractionally distilled (1 mbar, top temperature 70-90° C., bottom temperature up to 180° C.). The bottoms (1.9 kg) contained virtually all 1,4-cyclohexanediols.

As low boilers, 0.6 kg were distilled off (1,2-cyclohexanediols, valerolactone, methyl 5-hydroxyvalerate, dimethyl glutarate, dimethyl succinate, inter alia). As the fraction comprising predominantly dimethyl adipate and methyl 6-hydroxycaproate, 4.3 kg were obtained.

The top stream constituting the ester fraction is passed into hydrogenation stage 5.

Stage 5 (Hydrogenation):

4.3 kg of the $C_6$ ester fraction from stage 4 were hydrogenated continuously in a 25 ml reactor over a catalyst (catalyst, 70% by weight of CuO, 25% by weight of ZnO, 5% by weight of $Al_2O_3$) which had been activated beforehand at 180° C. in a hydrogen stream. The feed was 20 g/h, the pressure 220 bar and the temperature 220° C. The ester conversion was 99.5%; the 1,6-hexanediol selectivity was over 99%.

Alternatively, the ester fraction was hydrogenated continuously in a two-stage reactor battery (1st reactor: 2.5 l of catalyst, trickle mode, 250 bar, product recycling: feed=10: 1, 220-230° C.; 2nd reactor: 0.5 l of catalyst, trickle mode in straight pass, 260 bar, 220° C.). The catalyst used was a catalyst composed of CuO (60%), $Al_2O_3$ (30%) and $Mn_2O_3$ (10%) which had been activated beforehand at 180° C. The feed rate was 1 kg/h. At 99.5% conversion, the hexanediol selectivity was over 99%.

Stage 6 and 7 (Hexanediol Purification):

4.0 kg of the hydrogenation effluent from stage 5 were fractionally distilled (distillation still with attached 70 cm column having random packing, reflux ratio 2). At 1013 mbar, 1 kg of predominantly methanolic low boiler mixture were distilled off. After application of vacuum (20 mbar), predominantly the 1,2-cyclohexanediols and 1,5-pentanediol distilled off. Afterward (b.p. 146° C.), 1,6-hexanediol distilled off with a purity of 99.8%. (Residual content predominantly 1,5-pentanediol.)

Stage 11

1 kg of the methanol-low boiler mixture from stage 6, 7 and 7 kg/h from stage 3 were mixed to give a composition of 80% by weight, approx. 4.9% by weight of mTHF, about 1.5% by weight of THP and 12.1% by weight of mTHP. 600 g of this mixture were concentrated by a mass concentration factor (mass of alcohol-low boiler mixture used mass of retentate) of about 3.6 at a temperature of 30° C. in a stirred pressure cell, into which flat membranes having a free membrane surface of approx. 70 $cm^2$ can be installed, with a Desal 3 SE reverse osmosis membrane from GE Osminics, Minnetonka, USA, at a transmembrane pressure of 80 bar established by injecting nitrogen. The permeate obtained after membrane passage and the retained liquid (retentate) had the following composition.

TABLE 1

|  | Permeate [% by wt.] | Retentate [% by wt.] |
|---|---|---|
| Methanol | approx. 88.9 | approx. 58.9 |
| MTHF | approx. 3.5 | approx. 8.5 |
| THP | approx. 0.9 | approx. 3.0 |
| MTHP | approx. 6.1 | approx. 27.1 |
| Proportion by weight | 0.71 | 0.29 |

430 g of the permeate were obtained and were recycled into stage 2. The retentate was discarded.

What is claimed is:

1. A process for preparing 1,6-hexanediol from a carboxylic acid mixture comprising adipic acid, 6-hydroxycaproic acid and small amounts of 1,4-cyclohexanediols and is obtained as a by-product in the oxidation of cyclohexane to cyclohexanone/cyclohexanol with oxygen or oxygen-containing gases and by water extraction of the reaction mixture, by esterification of the acids with $C_1$- to $C_{10}$-alcohols and hydrogenation, in which
   a) the mono- and dicarboxylic acids present in the aqueous dicarboxylic acid mixture are reacted with a low molecular weight alcohol to give the corresponding carboxylic esters,
   b) the resulting esterification mixture is freed of excess alcohol and low boilers in a first distillation stage,
   c) a separation of the bottom product is carried out in a second distillation stage to form an ester fraction substantially free of 1,4-cyclohexanediols and a fraction comprising at least the majority of the 1,4-cyclohexanediols,
   d) the ester fraction substantially free of 1,4-cyclohexanediols is catalytically hydrogenated and
   e) 1,6-hexanediol is obtained in a purifying distillation stage from the hydrogenation effluent while removing an alcohol-low boiler mixture,
   which comprises removing alcohol by a membrane system from the mixtures, obtained after the esterification in stage b) and/or after the hydrogenation in stage e), of alcohols and low boilers and recycling it into the esterification.

2. The process according to claim 1, wherein alcohol is removed by a membrane system from the mixtures obtained in stage b) and stage e).

3. The process according to claim 1, wherein methanol is removed.

4. The process according to claim 1, wherein the membrane system consists of at least one membrane.

5. The process according to claim 1, wherein the transmembrane pressure differential is from 20 to 200 bar.

6. The process according to claim 1, wherein the temperature of the mixture obtained in stage b) and/or e), as the feed stream of the membrane separation, is from 20 to 90° C.

* * * * *